United States Patent [19]

Nicolotti et al.

[11] Patent Number: 4,659,839

[45] Date of Patent: Apr. 21, 1987

[54] COUPLING AGENTS FOR RADIOLABELED ANTIBODY FRAGMENTS

[75] Inventors: Robert A. Nicolotti, Ferguson; Richard T. Dean, Chesterfield, both of Mo.

[73] Assignee: Mallinckrodt, Inc., St. Louis, Mo.

[21] Appl. No.: 659,456

[22] Filed: Oct. 10, 1984

[51] Int. Cl.$^4$ .................. C07D 207/40; A61K 43/00; A61K 49/00; G01N 33/563

[52] U.S. Cl. .................................... 548/546; 424/1.1; 424/9; 436/512

[58] Field of Search ..................... 548/546; 424/1.1, 9; 436/512

[56] References Cited

U.S. PATENT DOCUMENTS 4,214,048  7/1980  Kitagawa ........................... 436/547
4,308,249  12/1981  Frank et al. ........................ 424/9 X

FOREIGN PATENT DOCUMENTS 0141762  11/1979  Japan .................................. 548/546
0141763  11/1979  Japan .................................. 548/546
2109407   6/1983  United Kingdom .

Primary Examiner—Christine M. Nucker
Assistant Examiner—Stephen C. Wieder
Attorney, Agent, or Firm—Bernard, Rothwell & Brown

[57] ABSTRACT

Bifunctional coupling agent for joining radionuclide metal ions to biologically useful molecules, including antibody Fab' fragments are disclosed. The coupling agents contain a maleimide moiety and a paramagnetic or radionuclide chelating moiety. The maleimide can be used to selectively bind to free sulfhydryl groups, or amine groups.

5 Claims, 1 Drawing Figure

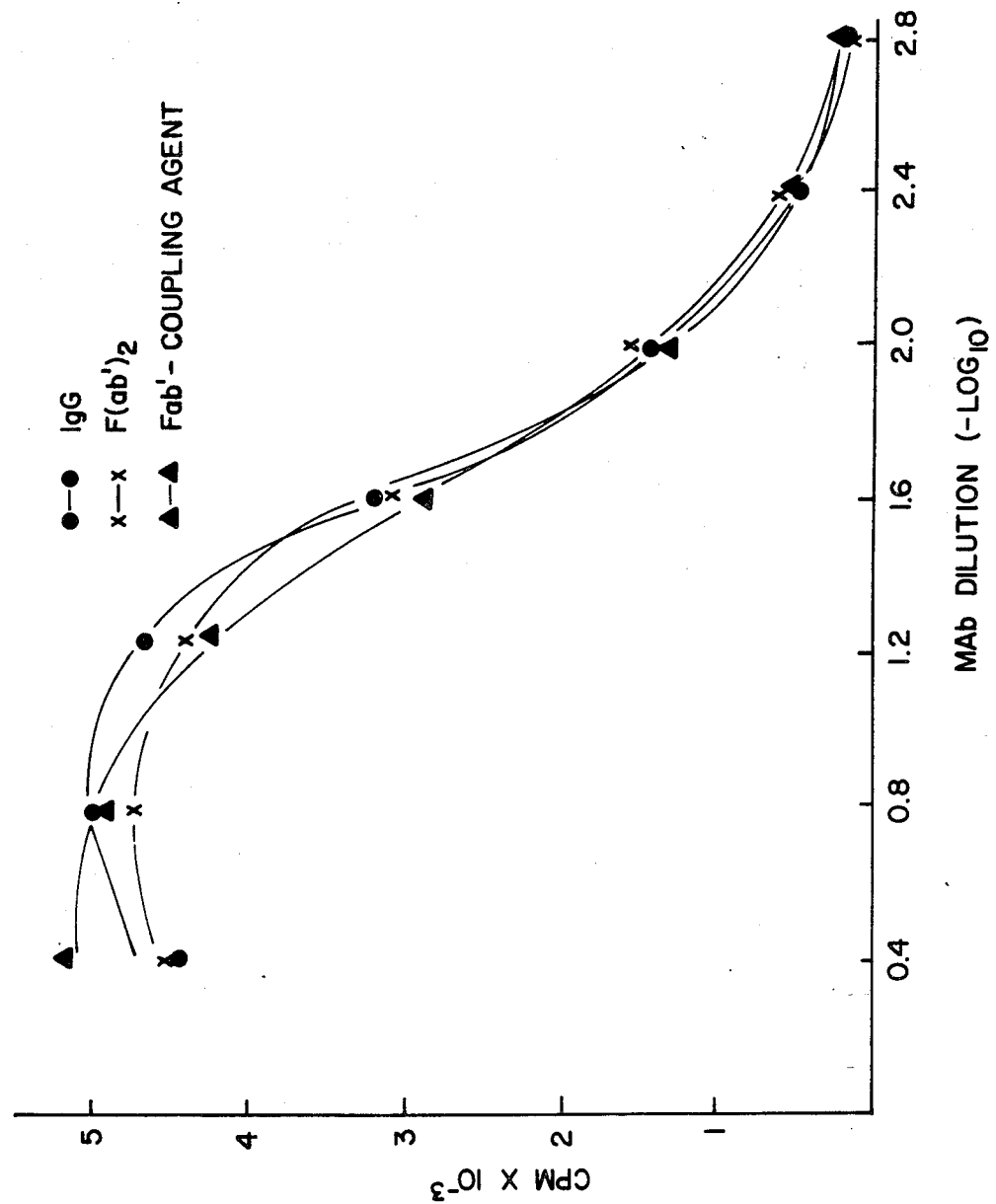

COUPLING AGENTS FOR RADIOLABELED ANTIBODY FRAGMENTS

BACKGROUND OF THE INVENTION

This invention relates to coupling agents useful in the production of biologically useful molecules labeled with metal ions. The ions may be either radiolabels or paramagnetic ions. Radiolabeled antibody fragments incorporating the coupling agents of the invention are useful in therapeutic and in vivo diagnostic applications. Paramagnetic labeled biologically useful molecules incorporating the coupling agents of the invention are useful in in vivo diagnostic applications.

Paramagnetic metals capable of influencing NMR relaxation properties for image enhancement have been known for some time, for example, Gd(III), Mn(II), Fe(III) and Cr(II).

The efficacy of paramagnetic metal ions in in vivo diagnostic applications depends on the ability to deliver the metal to the target site and have it influence the relaxation of the water in that region in an NMR imaging experiment.

The use of radionuclide metal ions in therapeutic and in vivo diagnostic applications has been practiced for some time. For example, gamma-emitting radionuclide metal ions, such as indium-111, gallium-67 and technetium-99m, have been used in diagnostic scintigraphy for tumor detection. Beta-emitting isotopes, such a rhenium-186, rhenium-188, rhenium-189, samarium-153, yttrium-90 and copper-67, can be used therapeutically in the treatment of tumors.

The efficacy of radionuclides in in vivo diagnostic and therapeutic applications depends on the ability to deliver the radionuclide to the site of the target cells. One method of delivering the radionuclide to the site of the target cells entails coupling the radionuclide metal ions to biologically useful molecules, such as antibodies, which selectively recognize and bind unique ligands associated with the target cells. For example, antigens which are known to be produced by or associated with malignant tumor cells can be bound by the antibody-conjugated radionuclide for the purpose of diagnostic imaging or for the purpose of irradiating the tumor to destroy it.

Goldenberg et al. (*N. Engl. J. Med.,* 298: 1384–1388 [1978]) describe experiments in which antibodies to carcinoembryonic antigen (CEA), which is a known tumor-associated antigen (Gold et al., *J. Exp. Med.,* 121: 439–462 [1965]), were labeled with iodine-131 and injected into patients with a history of cancer. After 48 hours, the patients were scanned with a gamma scintillation camera and tumors were localized by the gamma emission pattern. Similarly, United Kingdom Patent Application GB No. 2,109,407 describes the use of monoclonal antibodies to tumor-associated antigens, labeled with metallic radionuclides, for in vivo tumor detection and localization.

It has been suggested that radiolabeled antibody fragments, rather than radiolabeled whole antibodies, be used for in vivo diagnostic and therapeutic applications since the fragments may be better able to penetrate to the desired target site and the antibody fragments may minimize problems of immunogenicity and cross-reactivity associated with whole antibodies (see, e.g., U.S. Pat. No. 4,036,945; Lancet, Vol. II, No. 8087, 462 [1978]; Belitsky et al., *J. Nucl. Med.,* 19: 429 [1978]). Antibody fragments can be produced in several ways.

The antibody molecule can be enzymatically treated to remove carboxyl-terminal terminal portions of the heavy chains (the Fc fragment), leaving a bivalent F(ab')$_2$ fragment, i.e., two Fab' segments joined by one or more disulfide bonds which link the heavy chains. The F(ab')$_2$ fragment can then be selectively reduced at the disulfide bond(s) joining the two heavy chains, resulting in the production of two monovalent Fab' fragments each having a single antigen-binding site.

Antibody molecules contain a number of reactive side chains which can be employed as sites of attachment for binding a radionuclide metal ion to the antibody. For example, the radionuclide can be conjugated to the antibody through a linker molecule which is reactive with the carboxyl groups of aspartic acid or glutamic acid residues, the amino groups of lysine residues or the aromatic groups of tyrosine or histidine. Unfortunately, these residues are distributed randomly throughout the antibody molecule. Consequently, attachment of a radionuclide through these reactive groups can occur at any of a number of points along the antibody molecule. Attachment of the radionuclide-bearing moiety at or near the antigen binding site on the antibody molecule could inhibit the ability of the antibody to bind antigen, resulting in a loss or reduction of the effectiveness of the antibody-radionuclide conjugate as a diagnostic or therapeutic agent. There is needed a method of attaching a radionuclide to an antibody which does not have a significant adverse affect on the immunoreactivity of the antibody.

BRIEF DESCRIPTION OF THE DRAWING

The single FIGURE represents a series of binding curves in which the binding of an anti-CEA Fab'/Coupling Agent conjugate of the invention to human colon adenocarcinoma cell extracts is compared with that of intact monoclonal anti-DEA IgG and F(ab')$_2$ fragment.

SUMMARY OF THE INVENTION

This invention provides bifunctional coupling agents useful in forming conjugates with biologically useful molecules, such as antibodies, which can be coupled with paramagnetic or radionuclide metal ions to provide materials usful for in vivo diagnostic and therapeutic applications. The antibody conjugates, which are produced by reacting a bifunctional coupling agent of the invention with the free sulfhydryl group of an antibody Fab' fragment, retain the antigen-binding activity, i.e., immunoreactivity of the whole antibodies from which they are derived. The bifunctional coupling agent contains a maleimide group, which reacts specifically at pH 6–8 with the free sulfhydroxyl group of the Fab' fragment or with amines having pKa's $\leq 8$, and a group which is capable of forming a chelate complex with the paramagnetic or radionuclide metal ion. Alternatively, at more basic pH's, the maleimide can be made to react with amino groups of biologically useful molecules.

The antibody conjugates which incorporate the coupling agent of the invention can be represented by the general formula:

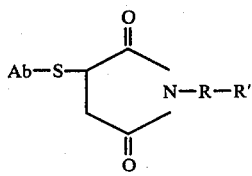

(I)

wherein Ab is the residue of a Fab' fragment of an antibody which retains antigen-binding activity following enzymatic removal of the Fc fragment and reductive cleavage of the disulfide bond joining the heavy chains; R is a divalent organic linker; and R' is a group which is capable of chelating a paramagnetic ion or radionuclide metal ion.

The antibody conjugate of formula I is complexed with a paramagnetic ion or radionuclide through the chelating group to form an antibody-radionuclide conjugate which can be employed therapeutically, e.g., in the treatment of malignant tumors, or as an in vivo diagnostic imaging agent.

DETAILED DESCRIPTION AND PREFERRED EMBODIMENTS

The antibody conjugates of formula I are prepared by reacting a bifunctional coupling agent of the invention with a Fab' fragment of an antibody. The Fab' fragment employed is derived from an antibody which is capable of retaining antigen-binding activity after it has undergone enzymatic and chemical treatments which convert the whole antibody to a Fab' fragment having at least one free sulfhydryl group. The whole antibody is first treated with an enzyme which effects a site-specific cleavage of the two heavy chains, removing the Fc portion at the carboxyl-terminal endss of the heavy chains. The resultant F(ab')2 antibody fragment is subjected to mild reducing conditions which preferably cleave the interchain disulfide bonds joining the two heavy chains, without concomitant cleavage of the intrachain disulfide bonds. There are thus produced two Fab' fragments, each having at least one free sulfhydryl group pendent from the heavy chans. The sulfhydryl group serves as a reactive site at which the Fab' fragment is joined to the coupling agent to produce the antibody conjugate. Since this site is located distant from the antigen-binding site, the conjugated coupling agent does not interfere with antigen binding.

As previously indicated, the Fab' fragments containing free sulfhydryl groups are produced by enzymatic removal of the Fc portion of whole antibodies followed by reduction of the resulting F(ab')2 dimer. It is desirable to prevent concomitant cleavage of the light-heavy chain disulfide bonds by carrying out the reduction under relatively mild chemical conditions which selectively reduce the interchain disulfide bonds between the two heavy chains. The antibody employed preferably has an enzymatic cleavage site which is situated such that removal of the Fc portion leaves the two halves of the F(ab')2 dimer joined by a single disulfide bond. The single disulfide bond can be preferentially cleaved under mild reducing conditions which do not disrupt the light-heavy chain bonds. Antibodies which are enzymatically cleaved, e.g., by pepsin or papain, to yield F(ab')2 dimers in which the two halves are joined by multiple disulfide bonds are generally non-preferred for use in the invention inasmuch as the relatively harsh chemical conditions which would be required to cleave the multiple bonds between the heavy chains would be likely to cleave the light-heavy chain bonds as well.

Antibodies which are enzymatically cleaved with papain in the presence of a thiol activating agent yield Fab fragments that are not useful in the invention inasmuch as the resulting antibody fragments lack free sulfhydryl groups which are necessary for coupling.

Antibodies which are useful in the practice of the invention include antibodies to any of the antigens which are known to be effective as in vivo tumor markers such as carcinoembryonic antigen, alpha-fetoprotein, human chorionic gonadotropin or its beta subunit, colon specific antigen-p, tumor specific glycoprotein and the like.

Antibodies of the subclass IgG$_1$ are preferred for use in the practice of the invention. This subclass of antibodies is the predominant subclass of monoclonal antibodies produced by hybridoma cells. The monoclonal antibody producing hybridoma cells are prepared by fusing a myeloma cell and an antibody-producing lymphocyte (G. Kohler and C. Millstein, *Nature* (London), 256: 495–497 [1975]). An example of an antibody for use in producing the Fab' fragments employed in the practice of the invention is an IgG$_1$ type monoclonal antibodies to the tumor associated antigen, CEA. This murine monoclonal anti-CEA antibody (subclass IgG$_1$) can be cleaved with preactivated thiol free papain, using the procedure of Parham, et al. (*J. Immunol. Methods*, 53: 133–173 [1982]) to produce an F(ab')2 fragment having a single disulfide bond joining the heavy chains. This fragment is then reduced, using a reducing agent such as 2-mercaptoethanol or cysteine, under mild reducing conditions which preferentially cleave the interchain disulfide bond joining the heavy chains to produce two Fab' fragments each having a single pendent sulfhydryl group. The reduction is conveniently carried out by incubation in a buffered solution at or near neutral pH. Temperature of the incubation is not critical and room temperature is suitable. Incubation is generally carried out for about 1 to 2 hours. Cysteine is the preferred reducing agent for the preferential cleavage of the interchain disulfide bond joining the heavy chains. The concentration of cysteine in the reduction reaction can be from about 2.5 to about 40 mM, preferably from 5 to 20 mM. At lower cysteine concentrations, substantial amounts of F(ab')2 are not reduced, while higher concentrations result in the undesired cleavage of the disulfide bonds joining the heavy and light chains.

The antibody conjugate of formula I is produced by reacting the Fab' fragment with a coupling agent of the invention which is represented by the formula:

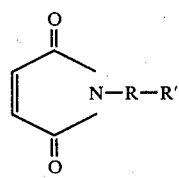

(II)

In formula II, R is a divalent organic radical which serves to join the maleimide group to the R' group. Any divalent organic radical which is nonreactive with the side chains on the antibody molecule can be employed. Preferably, R is —(CH$_2$)$_n$—, in which n is an integer from 1 to 20, or phenylene. For purposes of exemplification, R is —(CH$_2$)$_n$— in which n is 5 or 7.

R' is a group which is capable of chelating the paramagnetic or radionuclide metal ion. In selecting an appropriate chelating group, a number of criteria are taken into consideration. The chelating group should have a sufficiently high stability constant to minimize the exchange of the paramagnetic ion or radionuclide with circulating transferrin. The chelate complex should be thermodynamically stable under physiological conditions. It should be derived from a chelating agent which is non-toxic to the host. Moreover, the chelating group should be weakly acidic so that the molecular will partition extracellularly upon biocarrier degradation and subsequently be excreted in the urine.

The following are exemplary of coupling agents which can be employed to attach the radionuclide metal ion to the Fab' fragment:

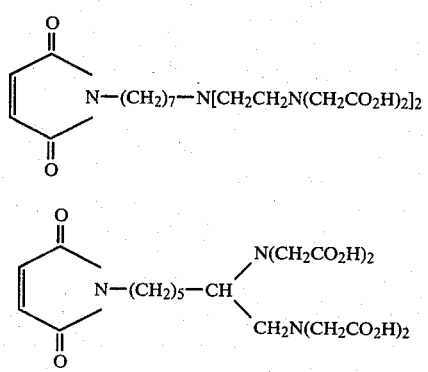

Compounds of the formula IIa and analogous compounds can be prepared in accordance with the following reaction scheme:

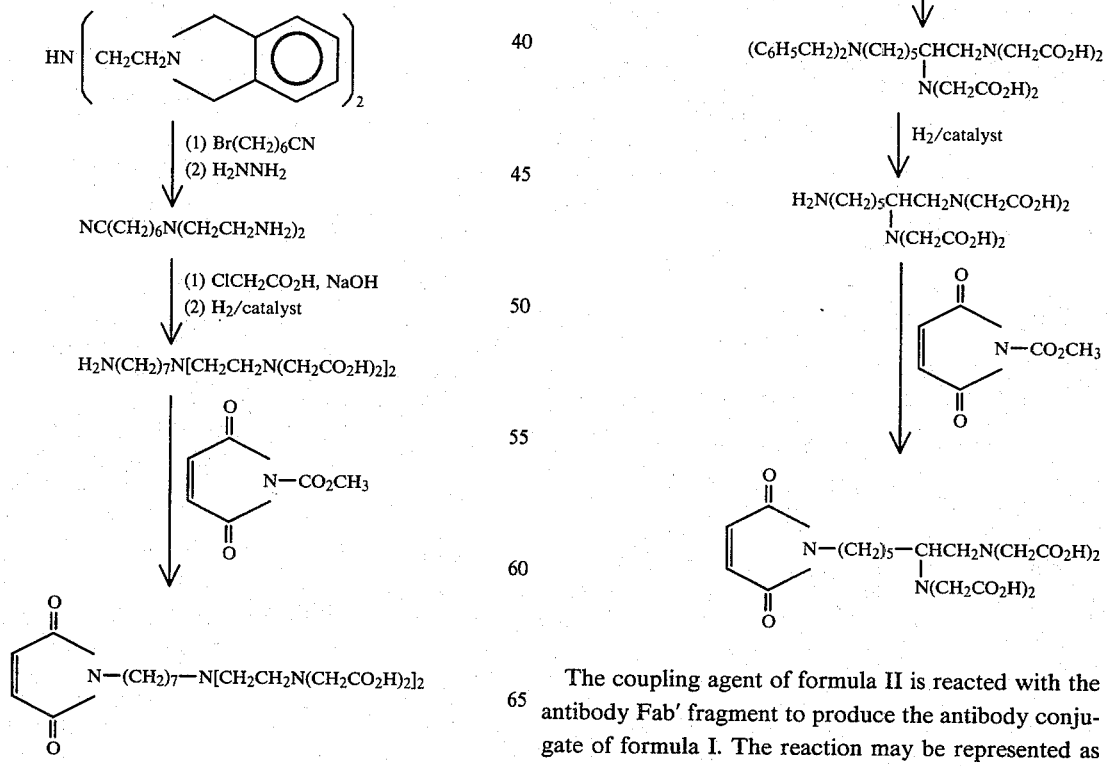

Compounds of formula IIb and analogous compounds can be prepared in accordance with the following reaction scheme:

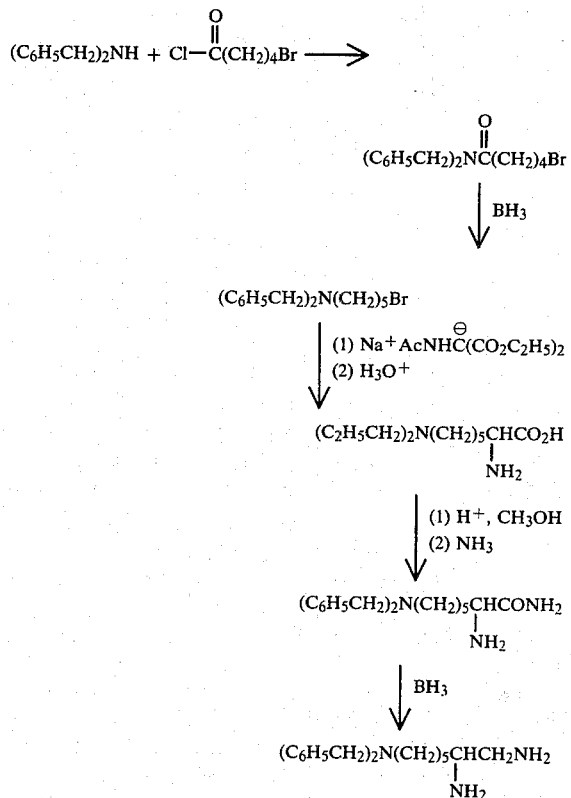

The coupling agent of formula II is reacted with the antibody Fab' fragment to produce the antibody conjugate of formula I. The reaction may be represented as follows:

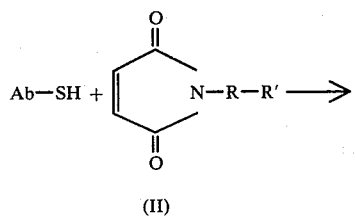

(II)

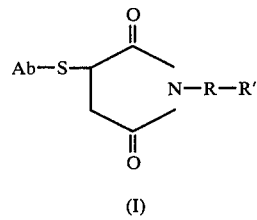

(I)

wherein Ab-SH represents the antibody Fab' fragment and R and R' have the previously defined meanings.

The reaction is carried out in a suitable buffer solution such as 20 mM phosphate, pH 7.0. Temperature of reaction is not critical and is preferably about room temperature. At room temperature, the reaction proceeds to completion in about 1 hour. The product can be isolated by conventional chromatographic means such as by chromatography on a DEAE column.

The antibody conjugate of formula I is complexed with a paramagnetic or radionuclide metal ion under chelating conditions. Any paramagnetic or radionuclide metal ion which is useful in therapeutic or in vivo diagnostic techniques and which one desires to bind to the antibody fragment can be employed. One can mention as merely exemplary of such paramagnetic ions gadolinium (III), iron (III), manganese (II) and chromium (II) and radionuclide metal ions gamma-emitting radionuclides useful in diagnostic scintigraphy such as indium-111, gallium-67 and technetium-99m, and beta-emitting nuclides useful in therapeutic applications such as yttrium-90 and copper-67, rhenium-186, rhenium-188, rhenium-189, samarium-153. Other useful classes of radionuclides include the alpha-emitting, positron-emitting and Auger-electron-emitting radionuclides. The complex can be formed by reacting the conjugate of formula I with the radionuclide in a buffered solution in which the conjugate is physiologically stable. If necessary, the paramagnetic or radionuclide can be provided to the solution as a complex with an intermediate chelating agent, i.e., a chelating agent which forms a chelate complex that renders the metal ion or radionuclide soluble at the physiological pH of the antibody conjugate but is less thermodynamically stable than the chelate complex which is formed with the antibody conjugate of formula I. For example, indium-111 is insoluble as the chloride salt in an antibody solution at physiological pH. It is preferred to provide the indium-111 to the chelation reaction in the form of an intermediate complex with 4,5-dihydroxy-1,3-benzene-disulfonic acid (Tiron), which renders the indium-111 soluble at physiological pH, but readily transfers the indium-111 to form a stable chelate complex with the antibody conjugate. Coupling of the paramagnetic ion or radionuclide to the antibody conjugate of formula I produces an antibody-radionuclide conjugate of the formula:

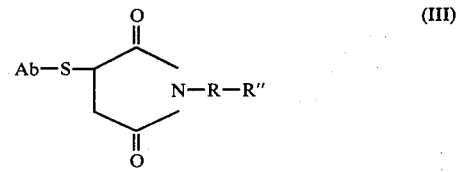

(III)

wherein Ab and R are as previously described and R" represents a chelate complex between the paramagnetic or radionuclide metal ion and the previously described group R'.

The antibody-metal ion conjugate of formula III can be formulated in a physiologically acceptable buffer for therapeutic or in vivo diagnostic use. In one embodiment of the invention, a Fab' fragment of a murine monoclonal antibody to CEA (subclass $IgG_1$) is conjugated to a coupling agent of formula II in which R is $-(CH_2)_7-$ and R' is the group $-N[CH_2CH_2N(CH_2CO_2H_2]_2$. The CEA-antibody conjugate is chelated with a gamma-emitting radionuclide such as indium-111 and employed as an in vivo tumor imaging agent using photoscanning procedures known in the art. The CEA-antibody-radionuclide conjugate is administered intravenously and the subject is subsequently photoscanned to determine the site of uptake of the radionuclide conjugate in vivo.

The following examples are intended to further illustrate the practice of the invention and are not intended to limit its scope in any way. In the examples, the following terms and abbreviations have the meanings indicated below:

| | |
|---|---|
| Coupling Agent | [((7-Maleimidoheptyl)imino)bis-(ethylenenitrilo)]tetraacetic acid |
| Mab | Monoclonal antibody |
| SDS | Sodium dodecylsulfate |
| EDTA | Ethylenediaminetetraacetic acid |
| $^3H$—NEM | N—[ethyl-2-$^3H$]—maleimide |
| MES | 2-N—morpholinoethansulfonic acid |
| Tiron | 4,5-Dihydroxy-1,3 benzene-disulfonic acid |
| IgGSORB | *Staphylococcus aureus*, strain. Cowan I formalin-fixed, heat-killed |

Iodination of Antigen

CEA was radiolabeled by the Iodogen method. 50 μg of antigen was added to a microfuge tube coated with 2 μg of Iodogen. One MCi of $Na^{125}I$ was added and incubated at 4° C. for fifteen minutes. After the incubation period, 20 μl of 10 mg/ml histidine was added to react with free iodine. Iodohistidine was removed by gel filtration on a Sephadex G-25M column (Pharmacia, Piscataway, N.J.).

Preparation of Human Colon Adenocarcinoma Cell Extracts

Cell extracts were prepared from colon adenocarcinoma. Tissues were minced and homogenized for 3 minutes at 4° C. in 10 mM tris-HCl (pH 7.2), 0.2 mM $CaCl^2$ (1 gm/10 ml), and then centrifuged at 1,000×g for 10 minutes. The pellet was resuspended in phosphate buffered saline and sonicated at 4° C. for 1 minute at 15 second intervals. The sonicate was centrifuged at 10,000×g for 15 minutes and the supernatant was used for solid phase radioimmunoassays (Example V).

EXAMPLE I

Preparation of [((7-Maleimidoheptyl)imino)bis(ethylenenitrilo)]tetraacetic Acid (a) Preparation of (6-cyanohexyl)bis(2-phthalimidoethyl)amine. A mixture of 6-bromohexylcyanide (13.88 g, 0.073 mol), bis(2-phthalimidoethyl)amine (26.52 g, 0.073 mol), and triethylamine (7.37 g, 0.073 mol) in DMF (120 ml) was heated at 100° C. for 20 hours. After cooling, the precipitate which had formed was removed by filtration and the filtrate was poured into ice (1000 ml). The aqueous solution was extracted with dichloromethane (3×200 ml). The combined organic extracts were washed with brine and dried over $Na_2SO_4$. Removal of the solvent under reduced pressure gave crude product which was chromatographed on silica gel (hexane—30% ethyl acetate/hexanes gradient elution). Impure fractions were rechromatographed to provide a total of 14.1 g of (6-cyanohexyl)bis(2-phthalimidoethyl)amine (41%) as an oil. The product was one spot on tlc. The ir spectrum was consistent with the assigned structure.

(b) Preparation of (6-Cyanohexyl)bis(2-aminoethyl)amine. A solution of (6-cyanohexyl)bis(2-phthalimidoethyl)amine (13.8 g, 0.029 mol) and hydrazine (2.15 g, 0.067 mol) in methanol (150 ml) was refluxed for 1.5 hours and allowed to stand overnight. The solvent was removed under reduced pressure and the residue was taken up in water (200 ml) and brought to $pH \approx 2$ with HCl. The precipitate was removed by filtration and the filtrate was made basic with solid NaOH. The solution was then concentrated under reduced pressure and extracted with dichloromethane (4×50 ml). The combined organic extracts were dried over $Na_2SO_4$ and evaporated under reduced pressure. Kugelrohr distillation of the residue gave pure (6-cyanohexyl)bis(2-aminoethyl)amine as a water white liquid (4.1 g—67%) collected between 120° and 140° C. (pot temp) at 0.07 mm Hg. The ir spectrum was consistent with the assigned structure, as was the elemental analysis.

(c) Preparation of [((6-Cyanohexyl)imino)bis(ethylenenitrilo)]tetraacetic Acid. A solution of chloroacetic acid (7.0 g, 0.074 mol) in water (20 ml) was neutralized by addition of the required amount of a solution of sodium hydroxide (5.92 g, 0.148 mol) in water (30 ml). (6-cyanohexyl)bis(2-aminoethyl)amine (3.72 g, 0.0175 mol) was added and the solution was heated at 45° C. for seven hours. During this time the pH of the solution was kept between 10 and 11 through addition of the remaining NaOH solution. After stirring at room temperature for two days the solution was brought to $pH \approx 7$ with concentrated HCl and the solvent was removed under reduced pressure. The residue was taken up in hot methanol (300 ml) and filtered. Removal of the methanol under reduced pressure gave crude [((6-cyanohexyl)imino)bis(ethylenenitrilo)]tetraacetic acid. This material was chromatographed in 2 g batches on a 2×30 cm column of BioRad AG 7×8 ion exchange resin in the formate form (gradient elution, 0–1M formic acid) to provide a total of 4.3 g (55%) of the tetraacid. The product was one spot on tlc (ethanol, 7% aqNH3, 4:1,—silica plate). The carbon nmr spectrum was consistent with the assigned structure.

(d) Preparation of [((7-Aminoheptyl)imino)bis(ethylenenitrilo)]tetraacetic Acid. A solution of [((6-cyanohexyl)imino)bis(ethylenenitrilo)]tetraacetic acid (0.85 g, 0.0019 mol) in acetic acid (50 ml) was treated with platinum oxide (0.15 g) and hydrogenated at 45 psi overnight. The catalyst was removed by filtration through celite and the filter pad was rinsed with water. The solvent was removed under reduced pressure to yield crude product, which was chromatographed on a Bio Rad AG 1×8 ion exchange resin in the formate form. Elution with water gave pure [((7-aminoheptyl)imino)bis(ethylenenitrilo)]tetraacetic acid (0.70 g, 82%). The product was one spot on tlc. The proton and carbon nmr spectra were consistent with the assigned structure.

(e) Preparation of [((7-Maleimidoheptyl)imino)bis(ethylenenitrilo)]tetraacetic acid. A solution of [((7-aminoheptyl)imino)bis(ethylenenitrilo)]tetraacetic acid (0.72 g, 1.6 mmol) in saturated aqueous sodium bicarbonate (15 ml) was cooled in an ice bath and N-carboxymethoxymaleimide (prepared according to *Helv. Chim. Acta,* 58, 531 [1975]) (0.25 g, 1.6 mmol) was added in one portion. After stirring 20 minutes the ice bath was removed and stirring was continued for 30 minutes. The solution was brought to $ph \approx 6$ with 1N HCl and concentrated under reduced pressure. The residue was chromatographed on a 2×30 cm column of Bio-Rad AG 1×8 ion exchange resin in the formate form (gradient elution, 0–1M formic acid) to provide 0.61 g of slightly impure product. This material was rechromatographed as above to yield pure [((7-maleimidoheptyl)imino)bis(ethylenenitrilo)]tetraacetic acid (0.42 g, 50%).

The product showed one spot on TLC (ethanol, 7% aqueous $NH_3$, 4:1 silica gel plate).

The maleimides could be detected on TLC as white spots on a bright yellow background by spraying with reagent A followed by reagent B.

Reagent A: 0.1% 5,5'-dithio-bis-2-nitrobenzoic acid (DTNB) in ethanol/tris-HCl buffer (pH 8.2), 1:1.

Reagent B: 2% sodium 2-mercaptoethanesulfonate in 80% aqueous ethanol.

EXAMPLE II

Preparation of Conjugate of Anti-CEA Fab' and [((7-Maleimidoheptyl)imino)bis(ethylenenitrilo)]tetraacetic Acid (a) Preparation of F(ab')2 fragment from anti-CEA monoclonal antibody (subclass $IgG_1$). Murine anti-CEA monoclonal antibody ($IgG_1$ subclass) was purified from ascitic fluid by $(NH_4)_2SO_4$ precipitation and ion-exchange chromatography. Enzymatic fragmentation of intact antibody, $IgG_1$, to yield F(ab')2 was accomplished by using thiolfree pre-activated papain according to Parham, et al., *J. Immunol. Methods,* 53: 133–173 (1982). Purified F(ab')2 fragment was obtained by sequential column chromatography over Whatman DE-52 and Sephadex G-100 resins. Denaturing gel electrophoresis (SDS-PAGE) showed the isolated protein to be greater than 95% pure.

(b) Determination of number of interchain disulfide bonds in F(ab')2 fragment. The F(ab')2 fragment generated by papain cleavage of the $IgG_1$ anti-CEA monoclonal antibody was determined ot have one interchain disulfide bond joining the two heavy chains. This determination was made by reducing the F(ab')2 antibody fragment with dithiothreitol under mild reducing conditions to rupture the interchain disulfide bonds joining the two heavy chains as well as the interchain disulfide bonds joining the heavy and light chains, while leaving the interchain disulfide bonds intact. The reduced fragments were then reacted with $^3$H-NEM—which reacts at the free sulfhydryl groups—and run on SDS-polyacrylamide gels, resulting in bands corresponding to heavy and light chains, each having its free sulfhydryl groups tritiated. The gel was protein stained, fluorophore soaked, dried and exposed to x-ray film to determine the relative intensity in the heavy and light chain bands. The fluor-soaked bands were excised and placed in scintillation counter. Using the counts per minute for the light chain band as a measure of one sulfhydryl group, the heavy chain was found to contain two sulfhydryls, one of which corresponds to the interchain disulfide bond with the light chain. Consequently, the other sulfhydryl corresponds to a single interchain disulfide bond between the heavy chains of the F(ab')$_2$ fragment produced by papain cleavage of the whole CEA antibody.

(c) Preparation of anti-CEA Fab' fragment. The anti-CEA F(ab')$_2$ fragment containing a single interchain disulfide bond joining the two heavy chains was reduced with cysteine under N$_2$ atmosphere at a protein concentration of 1 to 10 mg/ml. The optimal concentration of reductant and incubational time was determined such that greater than 85% of the F(ab')$_2$ was reduced to Fab' and less than 15% was reduced to individual light and heavy chains. Optimal reaction conditions were determined as follows.

F(ab')$_2$ fragments of monoclonal anti-CEA (subclass IgG$_1$) generated by papain-cleavage of whole antibody were reduced for 2 hours at room temperature in pH of approximately 7.4 buffer, using final cysteine concentrations of 0, 2.5, 5, 10, 15, 20, 25, 30, 35 and 40 mM. The resulting reduced fragments were reacted with NEM, which alkylates the free sulfhydryl groups in a manner analogous to the coupling agent, [((7-maleimidoheptyl)imino)bis(ethylenenitrilo)]tetraacetic acid. The reduced fragments produced with various concentrations of cysteine were run in separate lanes on SDS-polyacrylamide gels with whole antibody and F(ab')$_2$ fragment as controls, and the gels were protein stained. Observation of the stained gels indicated that, as cysteine concentration increased, the F(ab')$_2$ band gradually disappeared and a band corresponding in molecular weight to Fab' fragment appeared. Continued increase in the cysteine concentration resulted in the disappearance of the Fab' band, with concomitant appearance of two lower molecular weight bands corresponding to individual heavy and light chains. Optimal cysteine concentration, i.e., the concentration at which the F(ab')$_2$ band disappeared, but the individual heavy and light chain bands had not yet appeared, was found to be 10 mM.

Similar experiments resulted in typical cysteine concentrations (for optimum reduction of F(ab')$_2$ to Fab') of 5 mM to 15 mM and incubation times of 2 to 4 hours in the following N$_2$-bubbled buffers: 25 mM NaPO$_4$, 2 mM Na$_2$EDTA, 0.02% w/v NaN$_3$ pH 7.4; 57.4 mM Na$_2$HPO$_4$, 17.6 mM KH$_2$PO$_4$, 75 mM NaCl, 5 mM Na$_2$EDTA, 0.02% w/v NaN$_3$ pH 7.2 (RIA buffer); or 25 mM Tris, 2 mM Na$_2$EDTA, 0.02% w/v NaN$_3$, pH 8.0.

(d) Conjugation reaction. Reduced anti-CEA Fab' protein produced by the above-described procedure was freed of excess thiol reagent, under N$_2$ atmosphere, by exhaustive buffer exchange into 50 mM MES, 2 mM Na$_2$EDTA, pH 6.5 to 6.8, using diafiltration with a PM10 membrane. An aliquot of the resulting solution was tritrated with $^3$H-NEM of known specific activity to determine the number of free SH groups per Fab' molecule generated by the reduction procedure. The remainder was reacted with 10-25 mM of the coupling agent of Example I, i.e., [((7-maleimidoheptyl)imino)bis(ethylenenitrilo)]tetraacetic acid, for 2 to 4 hours at room temperature, then overnight at 4° C.

EXAMPLE III

Preparation of Chelate Complex of Indium-111 and Anti-CEA Fab' Conjugate

An antibody-radionuclide conjugate was prepared by adding 10 μl of $^{111}$InCl$_3$ (approximately 50 to 100 μCi) in 50 mM HCl (Rad-Pharm) to 5 μl of 10 mM Tiron, 4 mM HCl, pH 2.4, and incubating for 5 minutes at room temperature. There were then added 10 μl of 200 mM MES, pH 6.0, and 10 μl of 2-15 mg/ml of the conjugate of anti-CEA Fab' and Coupling Agent produced by the procedure of Example II. The reaction mixture was incubated for 1 hour at room temperature, after which 2-5 μl were spotted onto a cellulose acetate strip for electrophoretic analysis. Electrophoresis was conducted using 50 mM Hepes, pH 7.0, as the electrode buffer. In the electrophoretic field, the $^{111}$In-chelated anti-CEA Fab' conjugate remained at the origin and unreacted indium-111 migrated as a separate peak. In a separate electrophoresis, 7 μl of the chelte-conjugate reaction mixture was first incubated with 2 μl of 200 mM Na$_2$EDTA, pH 6.0, prior to electrophoresis. Addition of the EDTA caused a shift in the unreacted indium-111 peak but did not affect the chelate-conjugate peak, indicating that the chelated antibody conjugate was more stable than the $^{111}$In-Tiron chelate.

The anti-CEA Fab'/indium-111 conjugate can be administered intravenously in the form of a physiologically acceptable buffered solution for use as a tumor-imaging agent, for example, for imaging tumors of the colon using known photoscanning techniques.

EXAMPLE IV

Immunoaffinity of Conjugate of Anti-CEA Fab' and [((7-Maleimidoheptyl)imino)bis(ethylenenitrilo)]tetraacetic Acid The immunoaffinity of the monoclonal anti-CEA Fab'/Coupling Agent conjugate produced by the procedure of Example II was determined by radioimmunoassay with CEA antigen. IgGSORB (Staph A) (Enzyme Center, Boston, Mass.) coated with rat anti-mouse Kappa (300 μg of rat anti-mouse Kappa/1 ml of Staph A) was used to separate bound from free antigen. Serial dilutions of anti-CEA Fab'/Coupling Agent conjugate (protein concentration $3.7 \times 10^{-8}$M) were incubated overnight at room temperature with a fixed amount of $^{125}$I-labeled CEA antigen (218 ng) and varying amounts of unlabeled CEA antigen. Following incubation, 20 μl of coated IgGSORB were added to each well and the contents were incubated for 3 hours. The IgGSORB was washed 3 times by repetitive centrifugation and resuspension in RIA-buffer. The final pellet was placed in a gamma counter and analyzed for gamma emissions. As controls, radioimmunoassays were run in a similar manner using whole monoclonal anti-CEA IgG and F(ab')$_2$ fragment.

Binding curves (counts per minute vs. antibody dilution) were prepared for each antibody or fragment and for each concentration of unlabeled antigen. In each case, the addition of unlabeled CEA reduced the binding activity. Maximum binding for the monoclonal anti-CEA IgG was 30,000 cpm; for the anti-CEA F(ab')$_2$, 25,000 cpm; and for the monoclonal anti-CEA Fab'-/Coupling Agent conjugate, 19,000 cpm. Double reciprocal binding plots (1/bound vs. 1/free) were prepared for the antibody and fragments at various antibody dilutions. From the slopes and intercepts, the binding affinity was determined for each antibody or fragment and each dilution. The results, which are presented in Table I, indicate that the average binding affinity of the monoclonal anti-CEA Fab'/Coupling Agent conjugate was about the same as that of monoclonal anti-CEA IgG and anti-CEA F(ab')$_2$.

TABLE I

| Antibody | Dilution $-\text{Log}_{10}$ | Slope S | Y Intercept(Y) $(M^{-1})$ | Correlation Coefficient | Affinity Y/S $(M^{-1})$ | Average Affinity $(M^{-1})$ |
|---|---|---|---|---|---|---|
| IgG | 1.2 | 3.1 | $1.8 \times 10^9$ | 0.999 | $5.8 \times 10^8$ | $1 \times 10^9$ |
|  | 1.6 | 5.6 | $8.0 \times 10^9$ | 0.999 | $1.4 \times 10^9$ |  |
| F(ab')$_2$ | 0.8 | 4.2 | $3.8 \times 10^8$ | 0.995 | $0.9 \times 10^8$ |  |
|  | 1.2 | 2.9 | $3.6 \times 10^9$ | 0.989 | $1.2 \times 10^9$ | $1.5 \times 10^9$ |
|  | 1.6 | 4.2 | $10 \times 10^9$ | 0.989 | $2.5 \times 10^9$ |  |
| Fab'/Coupling Agent | 0.8 | 6.2 | $2.7 \times 10^9$ | 0.999 | $4.3 \times 10^8$ | $1.7 \times 10^9$ |
|  | 1.2 | 6.9 | $2 \times 10^{10}$ | 0.963 | $3 \times 10^9$ |  |

EXAMPLE V

Binding Profile in Solid Phase Radioimmunoassay

Fifty μl of human colon adenocarcinoma cell extracts were added to the well of polyvinyl plates and allowed to dry on an orbital aggitation plate. Then 200 μl of 1% bovine serum albumin (BSA) in phosphate buffered saline was added and incubated for 1 hour at room temperature. After the incubation period, 150 μl of the antibody (monoclonal anti-CEA IgG, F(ab')$_2$ fragment or anti-CEA Fab'/Coupling Agent conjugate) were added varying dilutions and incubated for another hour at room temperature. The wells were washed three times, and radioiodinated rat anti-mouse kappa was added and incubated for an hour. The wells were washed five times with phosphate buffer, and then analyzed for gamma emissions.

A binding curve (counters per minute vs. antibody dilution) was prepared for each antibody or fragment. The superimposed curves are presented in the Figure. It can be seen from the Figure that the monoclonal anti-CEA Fab'/Coupling Agent conjugate displayed a binding curve which was essentially identical to that of monoclonal anti-CEA IgG and anti-CEA F(ab')$_2$.

EXAMPLE VI

Biodistribution of In-111/Anti-CEA Fab' Conjugate and I-125 Nonspecific Fab' Fragments Female outbred Hsd athymic nude mice (nu/nu) were obtained from Harlin Sprague Dawley, Inc. (Indianapolis, Ind.) and inoculated subcutaneously with $10^7$ LS 174 CEA producing human tumor cells. After three (3) weeks when the tumors had reached approximately 6 grams, two (2) animals each were injected with either In-111 chelate labeled Fab' fragment of an anti-CEA monoclonal antibody produced as described in Example IV or the I-125 labeled Fab' fragment of an isotype matched nonspecific monoclonal antibody. Each group of animals received 12.5 Ci in one ml of phosphate buffered saline. After 24 hours, each animal was sacrificed and organs, tumor and blood were united by gamma scintigraphy. Table II shows the biodistribution of the specific In-111 labeled and nonspecific I-125 labeled antibody fragments. As can be seen, the specific labeled antibody fragment localized to the tumor 5.2 fold more than did the nonspecific antibody (localization index). The higher doses of In-111 in the kidney and liver are attributable to a more rapid clearance of I-125 than In-111 from these organs rather than differential uptake, as revealed from liver and kidney uptake and clearance kinetics (data not shown).

TABLE II

Biodistribution of In-111 Labeled Specific and I-125 Nonspecific Antibody Fab' Fragments in Tumor Bearing Nude Mice

|  | % Dose/Gram | |
|---|---|---|
|  | In-111 | I-125 |
| Tumor | 1.9 | .61 |
| Kidney | 72.0 | 28.0 |
| Liver | 4.3 | .53 |
| Lungs | 4.0 | 4.0 |
| Heart | .32 | .21 |
| Blood | .26 | .45 |
| Tumor/Blood | 7.3 | 1.4 |
| Localization Index |  | 5.2 |

What is claimed is:

1. A coupling agent for joining a paramagnetic or radionuclide metal ion with an antibody Fab' fragment comprising a compound of the formula:

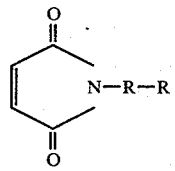

wherein R is selected from —(CH$_2$)$_n$— in which n is an integer from 1 to 20 and phenylene and R' is a group which is capable of chelating a radionuclide metal ion.

2. A coupling agent as claimed in claim 1, wherein R is —C$_7$H$_{14}$— or —C$_5$H$_{10}$—.

3. A coupling agent as claimed in claim 1 or 2 in which R' is selected from —N[CH$_2$CH$_2$N(CH$_2$CO$_2$H)$_2$]$_2$ and —CH[N(CH$_2$CO$_2$H)$_2$]CH$_2$N(CH$_2$CO$_2$H)$_2$.

4. A coupling agent for joining a paramagnetic or radionuclide metal ion with an antibody Fab' fragment comprising a compound of the formula:

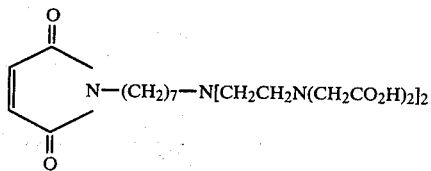
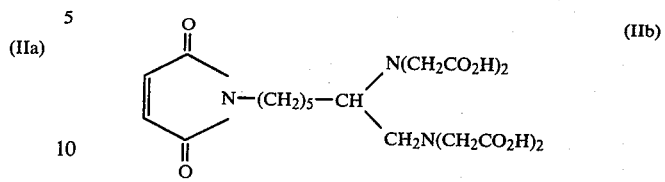
5. A coupling agent for joining a paramagnetic or radionuclide metal ion with an antibody Fab' fragment comprising a compound of the formula:
* * * * *

UNITED STATES PATENT AND TRADEMARK OFFICE
CERTIFICATE OF CORRECTION

PATENT NO. : 4,659,839

DATED : April 21, 1987

INVENTOR(S) : Robert A. Nicolotti et al.

It is certified that error appears in the above-identified patent and that said Letters Patent is hereby corrected as shown below:

In the specification, Column 2, line 2, delete "terminal";

Column 2, line 41, delete "anti-DEA" and substitute -- anti-CEA --;

Column 2, line 58, delete "sulfhydroxyl" and substitute -- sulfhydryl --;

Column 10, line 47, delete "F(ab!)$_2$ and substitute F(ab')$_2$ --;

Column 13, line 44, delete "counters" and substitute -- counts --

Signed and Sealed this

Twenty-sixth Day of April, 1988

*Attest:*

DONALD J. QUIGG

*Attesting Officer*  *Commissioner of Patents and Trademarks*